(12) United States Patent
Nita

(10) Patent No.: US 9,282,984 B2
(45) Date of Patent: Mar. 15, 2016

(54) THERAPEUTIC ULTRASOUND SYSTEM

(75) Inventor: Henry Nita, Redwood Shores, CA (US)

(73) Assignee: Flowcardia, Inc., Tempe, AZ (US)

( * ) Notice: Subject to any disclaimer, the term of this patent is extended or adjusted under 35 U.S.C. 154(b) by 701 days.

(21) Appl. No.: 11/398,385

(22) Filed: Apr. 5, 2006

(65) Prior Publication Data
US 2007/0239027 A1 Oct. 11, 2007

(51) Int. Cl.
*A61B 17/32* (2006.01)
*A61B 17/22* (2006.01)
*A61B 17/00* (2006.01)

(52) U.S. Cl.
CPC . *A61B 17/22012* (2013.01); *A61B 2017/00477* (2013.01)

(58) Field of Classification Search
CPC ............... A61B 17/22012; A61B 2017/22014; A61B 2017/22015; A61B 2017/22017; A61B 2017/22018
USPC ......... 600/466; 604/22, 21; 606/41, 169, 127, 606/128; 601/4
See application file for complete search history.

(56) References Cited

U.S. PATENT DOCUMENTS

| | | |
|---|---|---|
| 3,433,226 A | 3/1969 | Boyd |
| 3,565,062 A | 2/1971 | Kuris |
| 3,612,038 A | 10/1971 | Halligan |
| 3,631,848 A | 1/1972 | Muller |
| 3,719,737 A | 3/1973 | Vaillancourt et al. |
| 3,823,717 A | 7/1974 | Pohlman et al. |
| 3,839,841 A | 10/1974 | Amplatz |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance |

(Continued)

FOREIGN PATENT DOCUMENTS

| | | |
|---|---|---|
| DE | 2256127 | 5/1974 |
| DE | 2438648 | 2/1976 |

(Continued)

OTHER PUBLICATIONS http://www.merriam-webster.com/dictionary/couple, definition of the term coupled retrieved on May 18, 2013.*

(Continued)

*Primary Examiner* — David C Eastwood
(74) *Attorney, Agent, or Firm* — C.R. Bard Intellectual Property; Buchalter Nemer

(57) ABSTRACT

An ultrasound system has a catheter including an elongate flexible catheter body having at least one lumen extending longitudinally therethrough. An ultrasound transmission wire extends longitudinally through the lumen of the catheter body, and has a proximal region, a distal region, and an intermediate region between the proximal region and the distal region. A sonic connector is connected to the proximal region of the ultrasound transmission wire, and a distal head is positioned at the distal end of the catheter body and coupled to the distal region of the ultrasound transmission wire. The proximal region of the ultrasound transmission wire has a larger diameter than the intermediate region, the intermediate region is continuously tapered with a progressively decreasing diameter from its proximal end to its distal end, and the distal region has a greater diameter than the distal end of the intermediate region.

27 Claims, 3 Drawing Sheets

(56) References Cited

U.S. PATENT DOCUMENTS

| | | | |
|---|---|---|---|
| 4,417,578 A | | 11/1983 | Banko |
| 4,425,115 A | | 1/1984 | Wuchinich |
| 4,486,680 A | | 12/1984 | Bonnet et al. |
| 4,505,767 A | | 3/1985 | Quin |
| 4,565,589 A | | 1/1986 | Harrison |
| 4,572,184 A | * | 2/1986 | Stohl et al. .................. 606/128 |
| 4,664,112 A | | 5/1987 | Kensey et al. |
| 4,665,906 A | | 5/1987 | Jervis |
| 4,679,558 A | | 7/1987 | Kensey et al. |
| 4,700,705 A | | 10/1987 | Kensey et al. |
| 4,721,117 A | | 1/1988 | Mar et al. |
| 4,750,902 A | | 6/1988 | Wuchinich et al. |
| 4,808,153 A | | 2/1989 | Parisi |
| 4,811,743 A | | 3/1989 | Stevens |
| 4,827,911 A | | 5/1989 | Broadwin et al. |
| 4,838,853 A | | 6/1989 | Parisi |
| 4,854,325 A | | 8/1989 | Stevens |
| 4,870,953 A | | 10/1989 | DonMicheal et al. |
| 4,886,060 A | | 12/1989 | Wiksell |
| 4,920,954 A | | 5/1990 | Alliger et al. |
| 4,923,462 A | | 5/1990 | Stevens |
| 4,924,863 A | | 5/1990 | Sterzer |
| 4,931,047 A | * | 6/1990 | Broadwin et al. ............. 604/22 |
| 4,936,281 A | | 6/1990 | Stasz |
| 4,936,845 A | | 6/1990 | Stevens |
| 5,000,185 A | | 3/1991 | Yock |
| 5,015,227 A | | 5/1991 | Broadwin et al. |
| 5,026,384 A | | 6/1991 | Farr et al. |
| 5,046,503 A | | 9/1991 | Schneiderman |
| 5,053,008 A | | 10/1991 | Bajaj |
| 5,058,570 A | | 10/1991 | Idemoto et al. |
| 5,076,276 A | | 12/1991 | Sakurai |
| 5,091,205 A | | 2/1992 | Fan |
| 5,100,423 A | | 3/1992 | Fearnot |
| 5,109,859 A | | 5/1992 | Jenkins |
| 5,114,414 A | | 5/1992 | Buchbinder |
| 5,116,350 A | | 5/1992 | Stevens |
| 5,127,917 A | | 7/1992 | Niederhauser et al. |
| 5,156,143 A | | 10/1992 | Bocquet et al. |
| 5,163,421 A | | 11/1992 | Bernstein |
| 5,180,363 A | | 1/1993 | Idemoto et al. |
| 5,183,470 A | | 2/1993 | Wettermann |
| 5,195,955 A | | 3/1993 | Don Michael |
| 5,215,614 A | | 6/1993 | Wijkamp et al. |
| 5,221,255 A | | 6/1993 | Mahurkar et al. |
| 5,226,421 A | | 7/1993 | Frisbie et al. |
| 5,234,416 A | | 8/1993 | Macaulay et al. |
| 5,238,004 A | | 8/1993 | Sahatjian et al. |
| 5,242,385 A | | 9/1993 | Strukel |
| 5,243,997 A | | 9/1993 | Uflacker et al. |
| 5,248,296 A | | 9/1993 | Alliger |
| 5,255,669 A | | 10/1993 | Kubota et al. |
| 5,267,954 A | | 12/1993 | Nita |
| 5,269,291 A | * | 12/1993 | Carter ........................ 606/128 |
| 5,269,297 A | | 12/1993 | Weng et al. |
| 5,269,793 A | | 12/1993 | Simpson |
| 5,287,858 A | | 2/1994 | Hammerslag et al. |
| 5,290,229 A | | 3/1994 | Paskar |
| 5,304,115 A | | 4/1994 | Pflueger et al. |
| 5,304,131 A | | 4/1994 | Paskar |
| 5,312,328 A | | 5/1994 | Nita et al. |
| 5,318,014 A | * | 6/1994 | Carter ........................ 606/128 |
| 5,318,570 A | | 6/1994 | Hood et al. |
| 5,324,255 A | | 6/1994 | Passafaro et al. |
| 5,324,260 A | | 6/1994 | O'Neill et al. |
| 5,325,860 A | | 7/1994 | Seward et al. |
| 5,326,342 A | | 7/1994 | Pflueger et al. |
| 5,341,818 A | | 8/1994 | Abrams et al. |
| 5,342,292 A | | 8/1994 | Nita et al. |
| 5,344,395 A | | 9/1994 | Whalen et al. |
| 5,346,502 A | | 9/1994 | Estabrook et al. |
| 5,362,309 A | | 11/1994 | Carter |
| 5,368,557 A | | 11/1994 | Nita |
| 5,368,558 A | | 11/1994 | Nita |
| 5,376,084 A | | 12/1994 | Bacich et al. |
| 5,378,234 A | | 1/1995 | Hammerslag et al. |
| 5,380,274 A | * | 1/1995 | Nita ............................... 604/22 |
| 5,380,316 A | | 1/1995 | Aita et al. |
| 5,382,228 A | | 1/1995 | Nita et al. |
| 5,383,460 A | | 1/1995 | Jang et al. |
| 5,389,096 A | | 2/1995 | Aita et al. |
| 5,397,293 A | | 3/1995 | Alliger et al. |
| 5,397,301 A | | 3/1995 | Pflueger et al. |
| 5,405,318 A | | 4/1995 | Nita |
| 5,409,483 A | * | 4/1995 | Campbell et al. .............. 606/15 |
| 5,417,672 A | | 5/1995 | Nita et al. |
| 5,417,703 A | | 5/1995 | Brown et al. |
| 5,421,923 A | | 6/1995 | Clarke et al. |
| 5,427,118 A | | 6/1995 | Nita et al. |
| 5,431,168 A | | 7/1995 | Webster, Jr. |
| 5,431,663 A | | 7/1995 | Carter |
| 5,443,078 A | | 8/1995 | Uflacker |
| 5,447,509 A | | 9/1995 | Mills et al. |
| 5,449,369 A | | 9/1995 | Imran |
| 5,451,209 A | | 9/1995 | Ainsworth et al. |
| 5,465,733 A | | 11/1995 | Hinohara et al. |
| 5,474,531 A | * | 12/1995 | Carter ............................ 604/22 |
| 5,480,379 A | | 1/1996 | La Rosa |
| 5,484,398 A | | 1/1996 | Stoddard |
| 5,487,757 A | | 1/1996 | Truckai et al. |
| 5,507,738 A | | 4/1996 | Ciervo |
| 5,516,043 A | | 5/1996 | Manna et al. |
| 5,527,273 A | | 6/1996 | Manna et al. |
| 5,540,656 A | | 7/1996 | Pflueger et al. |
| 5,542,917 A | | 8/1996 | Nita et al. |
| 5,597,882 A | | 1/1997 | Schiller et al. |
| 5,607,421 A | | 3/1997 | Jeevanandam et al. |
| 5,611,807 A | | 3/1997 | O'Boyle |
| 5,618,266 A | | 4/1997 | Liprie |
| 5,626,593 A | | 5/1997 | Imran |
| 5,649,935 A | | 7/1997 | Kremer et al. |
| 5,658,282 A | | 8/1997 | Daw et al. |
| 5,695,460 A | * | 12/1997 | Siegel et al. .................... 604/21 |
| 5,695,507 A | | 12/1997 | Auth et al. |
| 5,715,825 A | | 2/1998 | Crowley |
| 5,720,724 A | | 2/1998 | Ressemann et al. |
| 5,728,062 A | | 3/1998 | Brisken |
| 5,738,100 A | | 4/1998 | Yagami et al. |
| 5,797,876 A | | 8/1998 | Spears et al. |
| 5,816,923 A | | 10/1998 | Milo et al. |
| 5,827,203 A | | 10/1998 | Nita |
| 5,830,222 A | | 11/1998 | Makower |
| 5,846,218 A | | 12/1998 | Brisken et al. |
| 5,895,397 A | | 4/1999 | Jang et al. |
| 5,902,287 A | | 5/1999 | Martin |
| 5,904,667 A | | 5/1999 | Falwell |
| 5,935,142 A | * | 8/1999 | Hood ........................... 606/169 |
| 5,935,144 A | | 8/1999 | Estabrook |
| 5,944,737 A | | 8/1999 | Tsonton et al. |
| 5,957,882 A | | 9/1999 | Nita et al. |
| 5,957,899 A | | 9/1999 | Spears et al. |
| 5,964,223 A | | 10/1999 | Baran |
| 5,967,984 A | | 10/1999 | Chu et al. |
| 5,971,949 A | | 10/1999 | Levin et al. |
| 5,976,119 A | | 11/1999 | Spears et al. |
| 5,989,208 A | * | 11/1999 | Nita ............................... 604/22 |
| 5,997,497 A | | 12/1999 | Nita et al. |
| 6,004,280 A | | 12/1999 | Buck et al. |
| 6,007,499 A | | 12/1999 | Martin et al. |
| 6,007,514 A | | 12/1999 | Nita |
| 6,022,309 A | | 2/2000 | Celliers et al. |
| 6,029,671 A | | 2/2000 | Stevens et al. |
| 6,030,357 A | | 2/2000 | Daoud et al. |
| 6,051,010 A | | 4/2000 | DiMatteo et al. |
| 6,113,558 A | | 9/2000 | Rosenschein et al. |
| 6,123,698 A | | 9/2000 | Spears et al. |
| 6,149,596 A | | 11/2000 | Bancroft |
| 6,159,176 A | | 12/2000 | Broadwin et al. |
| 6,165,127 A | | 12/2000 | Crowley |
| 6,165,188 A | | 12/2000 | Saadat et al. |
| 6,179,809 B1 | | 1/2001 | Khairkhahan et al. |
| 6,190,353 B1 | | 2/2001 | Makower et al. |
| 6,206,842 B1 | | 3/2001 | Tu et al. |
| 6,210,356 B1 | | 4/2001 | Anderson et al. |

(56) References Cited

U.S. PATENT DOCUMENTS

| | | |
|---|---|---|
| 6,217,543 B1 | 4/2001 | Anis et al. |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,302,875 B1 | 10/2001 | Makower et al. |
| 6,309,358 B1 | 10/2001 | Okubo |
| 6,315,741 B1 | 11/2001 | Martin et al. |
| 6,379,378 B1 | 4/2002 | Werneth et al. |
| 6,387,109 B1 | 5/2002 | Davison et al. |
| 6,394,956 B1 | 5/2002 | Chandrasekaran et al. |
| 6,398,736 B1 | 6/2002 | Seward |
| 6,416,533 B1 | 7/2002 | Gobin et al. |
| 6,423,026 B1 | 7/2002 | Gesswein et al. |
| 6,433,464 B2 | 8/2002 | Jones |
| 6,434,418 B1 | 8/2002 | Neal et al. |
| 6,450,975 B1 | 9/2002 | Brennan et al. |
| 6,454,757 B1 | 9/2002 | Nita et al. |
| 6,454,997 B1 | 9/2002 | Divino, Jr. et al. |
| 6,484,052 B1 | 11/2002 | Visuri et al. |
| 6,491,707 B2 | 12/2002 | Makower |
| 6,494,891 B1 | 12/2002 | Cornish et al. |
| 6,508,781 B1 | 1/2003 | Brennan et al. |
| 6,508,784 B1 | 1/2003 | Shu |
| 6,511,458 B2 | 1/2003 | Milo et al. |
| 6,524,251 B2 | 2/2003 | Rabiner et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,558,502 B2 | 5/2003 | Divino, Jr. et al. |
| 6,562,031 B2 * | 5/2003 | Chandrasekaran et al. .... 606/41 |
| 6,589,253 B1 | 7/2003 | Cornish et al. |
| 6,596,235 B2 | 7/2003 | Divino, Jr. et al. |
| 6,615,062 B2 | 9/2003 | Ryan et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner |
| 6,676,900 B1 | 1/2004 | Divino, Jr. et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,725 B2 | 4/2004 | Milo et al. |
| 6,729,334 B1 | 5/2004 | Baran |
| 6,733,451 B2 | 5/2004 | Rabiner et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,896,659 B2 * | 5/2005 | Conston et al. ............. 600/458 |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 7,004,173 B2 | 2/2006 | Sparks et al. |
| 7,056,294 B2 | 6/2006 | Khairkhahan et al. |
| 7,131,983 B2 | 11/2006 | Murakami |
| 7,137,963 B2 | 11/2006 | Nita et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,335,180 B2 | 2/2008 | Nita et al. |
| 7,341,569 B2 * | 3/2008 | Soltani et al. .................... 604/22 |
| 7,384,407 B2 | 6/2008 | Rodriguez et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,929 B2 | 11/2009 | Nita et al. |
| 7,776,025 B2 | 8/2010 | Bobo, Jr. |
| 7,938,819 B2 | 5/2011 | Kugler et al. |
| 7,955,293 B2 | 6/2011 | Nita et al. |
| 8,043,251 B2 | 10/2011 | Nita et al. |
| 8,083,727 B2 | 12/2011 | Kugler et al. |
| 8,226,566 B2 | 7/2012 | Nita |
| 2002/0107473 A1 * | 8/2002 | Bond et al. ........................ 604/22 |
| 2003/0009153 A1 * | 1/2003 | Brisken et al. ............. 604/890.1 |
| 2003/0036705 A1 | 2/2003 | Hare et al. |
| 2003/0125620 A1 | 7/2003 | Satou et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0138563 A1 * | 7/2004 | Moehring et al. ............. 600/439 |
| 2004/0204670 A1 * | 10/2004 | Nita et al. ........................ 604/22 |
| 2005/0215946 A1 * | 9/2005 | Hansmann et al. ............. 604/66 |
| 2005/0222557 A1 | 10/2005 | Baxter et al. |
| 2005/0228286 A1 | 10/2005 | Messerly et al. |
| 2006/0264759 A1 * | 11/2006 | Moehring et al. ............. 600/469 |
| 2006/0264809 A1 * | 11/2006 | Hansmann et al. ............. 604/22 |
| 2007/0037119 A1 | 2/2007 | Pal et al. |
| 2007/0260172 A1 | 11/2007 | Nita |
| 2008/0108937 A1 | 5/2008 | Nita |
| 2008/0208109 A1 * | 8/2008 | Soltani et al. .................... 604/22 |
| 2008/0221506 A1 * | 9/2008 | Rodriguez et al. .............. 604/22 |
| 2008/0228111 A1 * | 9/2008 | Nita .................................. 601/3 |
| 2011/0130834 A1 | 6/2011 | Wilson et al. |

FOREIGN PATENT DOCUMENTS

| | | |
|---|---|---|
| DE | 3821836 | 1/1990 |
| DE | 8910040 | 1/1990 |
| DE | 4042435 | 8/1991 |
| EP | 0005719 | 12/1979 |
| EP | 0316789 | 5/1989 |
| EP | 0376562 | 7/1990 |
| EP | 0379156 | 7/1990 |
| EP | 0394583 | 10/1990 |
| EP | 0443256 | 8/1991 |
| EP | 0541249 | 5/1993 |
| EP | 0820728 | 1/1998 |
| EP | 1323481 A2 | 7/2003 |
| GB | 1106957 | 3/1968 |
| JP | 01099547 | 4/1989 |
| JP | 2-71510 | 5/1990 |
| JP | U03067608 | 7/1991 |
| JP | 2006086822 | 3/1994 |
| JP | 2007116260 | 5/1995 |
| JP | 10216140 | 8/1998 |
| JP | 2001104356 | 4/2001 |
| JP | 2001321388 | 11/2001 |
| JP | 2002186627 | 7/2002 |
| JP | 2005-253874 | 9/2005 |
| WO | WO8906515 | 7/1989 |
| WO | 9001300 | 2/1990 |
| WO | 9004362 | 5/1990 |
| WO | 9107917 | 6/1991 |
| WO | WO9211815 | 7/1992 |
| WO | WO9308750 | 5/1993 |
| WO | 9316646 | 9/1993 |
| WO | WO9412140 | 6/1994 |
| WO | 9414382 | 7/1994 |
| WO | WO9508954 | 4/1995 |
| WO | WO9509571 | 4/1995 |
| WO | WO 95/15192 | 6/1995 |
| WO | WO9635469 | 11/1996 |
| WO | WO 97/21462 | 6/1997 |
| WO | WO9745078 | 12/1997 |
| WO | WO 98/52637 | 11/1998 |
| WO | WO9925412 | 5/1999 |
| WO | WO0053341 A1 | 9/2000 |
| WO | WO00/67830 | 11/2000 |

(56) References Cited

FOREIGN PATENT DOCUMENTS

| WO | WO2004012609 | 2/2004 |
| WO | WO 2004/112888 A2 | 12/2004 |
| WO | WO 2006/049593 | 5/2006 |

OTHER PUBLICATIONS http://www.thefreedictionary.com/connected, retrieved on Sep. 21, 2013.*

Siegel, et al., "In Vivo Ultrasound Arterial Recanalization of Atherosclerotic Total Occlusions", Journal of the American College of Cardiology, Feb. 1990, vol. 15, No. 2, pp. 345-351.

Extended European Search Report dated Mar. 5, 2012 for European Application No. 12153606.4.

Health Care Without Harm [report], Non-Incineration Medical Waste Treatment Technologies, "Irradiation, biological, and other technologies: E-beam, biological, and sharps treatment systems", Chapter 9., Aug. 2001, pp. 69-74.

Chandra Sehgal et al., Ultrasound-Assisted Thrombolysis, Investigative Radiology, 1993, vol. 28, Issue 10, pp. 939-943.

http://www.merriam-webster.com/dictionary/couple, definition of the term coupled retrieved on, May 18, 2013.

Margaret Fyfe et al., Mast cell degranulation and increased vascular permeability induced by 'therapeutic' ultrasound in the rate ankle joint, Br. J. exp. Path., 1984, vol. 65, pp. 671-676.

* cited by examiner

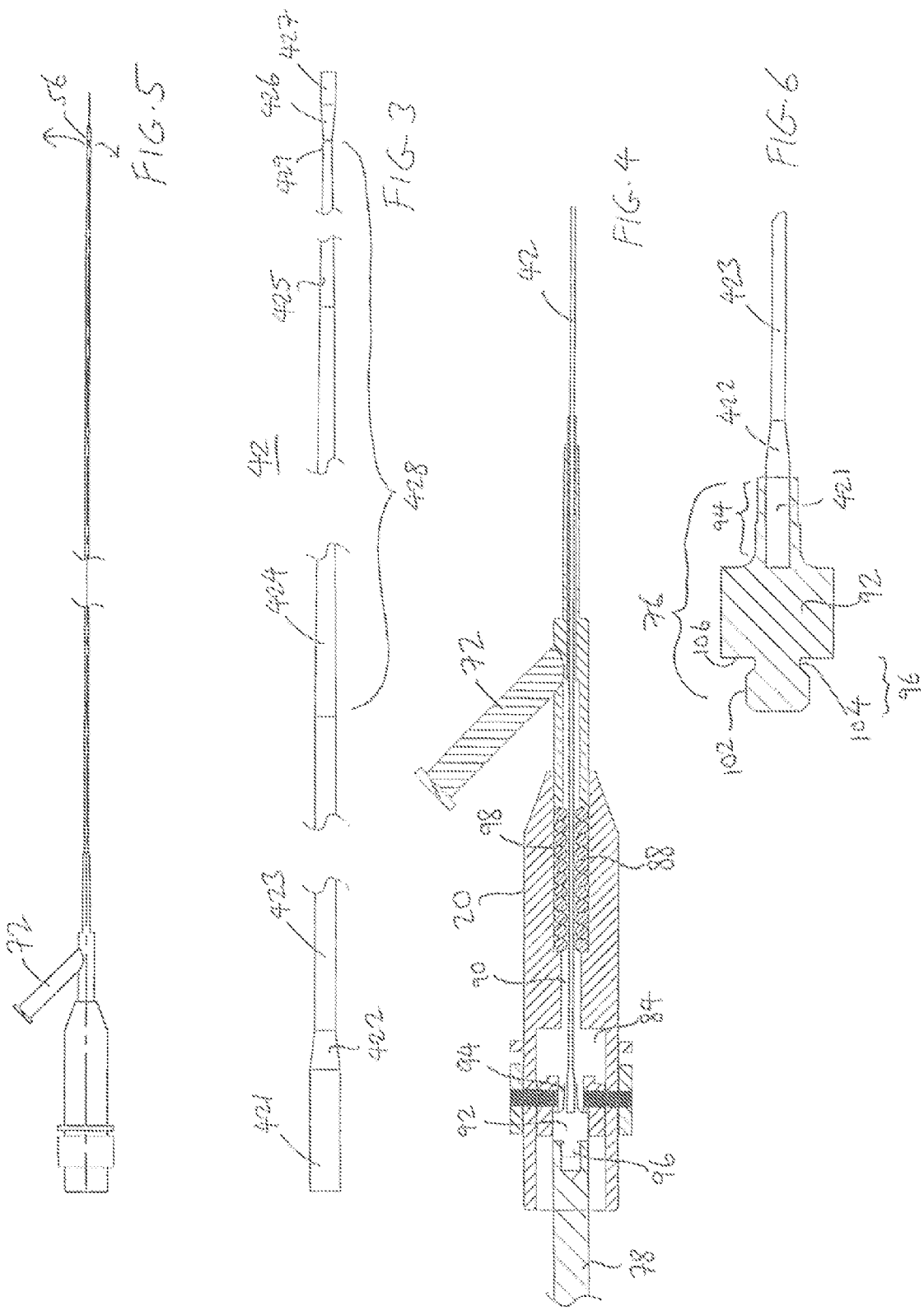

THERAPEUTIC ULTRASOUND SYSTEM

BACKGROUND OF THE INVENTION

1. Field of the Invention

The present invention pertains to medical equipment, and more particularly, to a therapeutic ultrasound system for ablating obstructions within tubular anatomical structures such as blood vessels.

2. Description of the Prior Art

A number of ultrasound systems and devices have heretofore been proposed for use in ablating or removing obstructive material from blood vessels. However, all of these systems and devices generally encounter three types of problems which are not always adequately addressed by these systems and devices.

One type of problem relates generally to the effective transmission of ultrasound energy from an ultrasound source to the distal tip of the device where the ultrasound energy is applied to ablate or remove obstructive material. Since the ultrasound source, such as a transducer, is usually located outside the human body, it is necessary to deliver the ultrasound energy over a long distance, such as about 150 cm, along an ultrasound transmission wire from the source to the distal tip. Attenuation of the acoustical energy along the length of the transmission wire means that the energy reaching the distal tip is reduced. To ensure that sufficient energy reaches the distal tip, a greater amount of energy must be delivered along the transmission wire from the source to the distal tip. This transmission of increased energy along the transmission wire may increase the fatigue experienced by the transmission wire at certain critical locations, such as at the connection between the transducer and the transmission wire. This fatigue and any associated stress may cause the transmission wire to break.

In this regard, the size of the proximal end of the transmission wire cannot be large. The proximal end of the transmission wire is usually bent while moving the ultrasound catheter back and forth during interventional procedures. A larger proximal end for a transmission wire will cause higher attenuation than a smaller proximal end, and provides a larger mass to expand and contract during the delivery of ultrasound energy.

Another type of problem relates to the heat that is built up from the transmission of ultrasound energy along the transmission wire. Many ultrasound transmission wires are made of superelastic alloys which exhibit elasticity within a specific temperature range, usually between 10 degrees Celsius and 50 degrees Celsius. However, during the delivery of ultrasound energy, the temperature of the transmission wire may reach 100 to 200 degrees Celsius, at which the transmission wire may lose its superelasticity and may experience mechanical deformations at portions that are bent when exposed to the high temperatures. The high temperatures may also cause the propagated energy to be lost more rapidly and transferred to heat, thereby reducing the efficacy of the ultrasound transmission wire.

Conventional ultrasound systems typically infuse a coolant fluid (usually 0.9% NaCl solution) through the irrigation lumen of an ultrasound catheter to bathe the transmission wire. To maintain the transmission wire within the desired temperature range of 10-50 degrees Celsius, the irrigation rate of the coolant fluid needs to be dramatically increased. However, there are two limitations to this approach. First, endovascular catheters usually have small inner and outer diameters that range between 0.5 to 3 mm. Therefore, the volume of fluid that can be delivered through the catheter is relatively small. Second, there is a limit to the amount of irrigant that can be delivered and left in the body of the patient during any interventional procedure, and this amount of irrigant should not exceed 500-1,000 $cm^3$. In addition to these two limitations, increased irrigation fluid pressure may cause local tissue damage.

Thus, there still exists a need in the art for improved ultrasound systems having ultrasound devices or catheters which address the aforementioned problems.

SUMMARY OF THE DISCLOSURE

It is an object of the present invention to provide an improved transmission wire for an ultrasound device.

It is another object of the present invention to provide an improved way of cooling the transmission wire of an ultrasound device during an interventional procedure.

In order to accomplish the objects of the present invention, there is provided an ultrasound system having a catheter including an elongate flexible catheter body having at least one lumen extending longitudinally therethrough. An ultrasound transmission wire extends longitudinally through the lumen of the catheter body, and has a proximal region, a distal region, and an intermediate region between the proximal region and the distal region. A sonic connector is connected to the proximal region of the ultrasound transmission wire, and a distal head is positioned at the distal end of the catheter body and coupled to the distal region of the ultrasound transmission wire. The proximal region of the ultrasound transmission wire has a larger diameter than the intermediate region, the intermediate region is continuously tapered with a progressively decreasing diameter from its proximal end to its distal end, and the distal region has a greater diameter than the distal end of the intermediate region.

The present invention also discloses a method for disrupting an occlusion in a blood vessel, which includes positioning an ultrasound catheter in a blood vessel such that a distal end of the catheter is adjacent an occlusion, introducing refrigerated irrigation fluid through the catheter, and transmitting ultrasound energy through the ultrasound catheter to disrupt the occlusion into multiple occlusion fragments.

The present invention also discloses a method for disrupting an occlusion in a blood vessel, which includes positioning an ultrasound catheter in a blood vessel such that a distal end of the catheter is adjacent the occlusion, transmitting ultrasound energy through the ultrasound catheter to disrupt the occlusion into multiple occlusion fragments, and introducing microbubbles around the distal end of the catheter during the transmission of ultrasound energy.

BRIEF DESCRIPTION OF THE DRAWINGS

FIG. 3 is a side sectional view of an ultrasound transmission wire that can be used with the system of FIG. 1.

FIG. 4 is a cross-sectional view of the proximal end of the catheter of FIG. 2 showing the connection of the ultrasound transmission wire of FIG. 3 to a sonic connector.

FIG. 5 is a side view of the catheter of FIG. 2.

FIG. 6 is a cross-sectional view of the sonic connector of the system of FIG. 1.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

In certain instances, detailed descriptions of well-known devices, compositions, components, mechanisms and methods are omitted so as to not obscure the description of the present invention with unnecessary detail.

Figure 1:
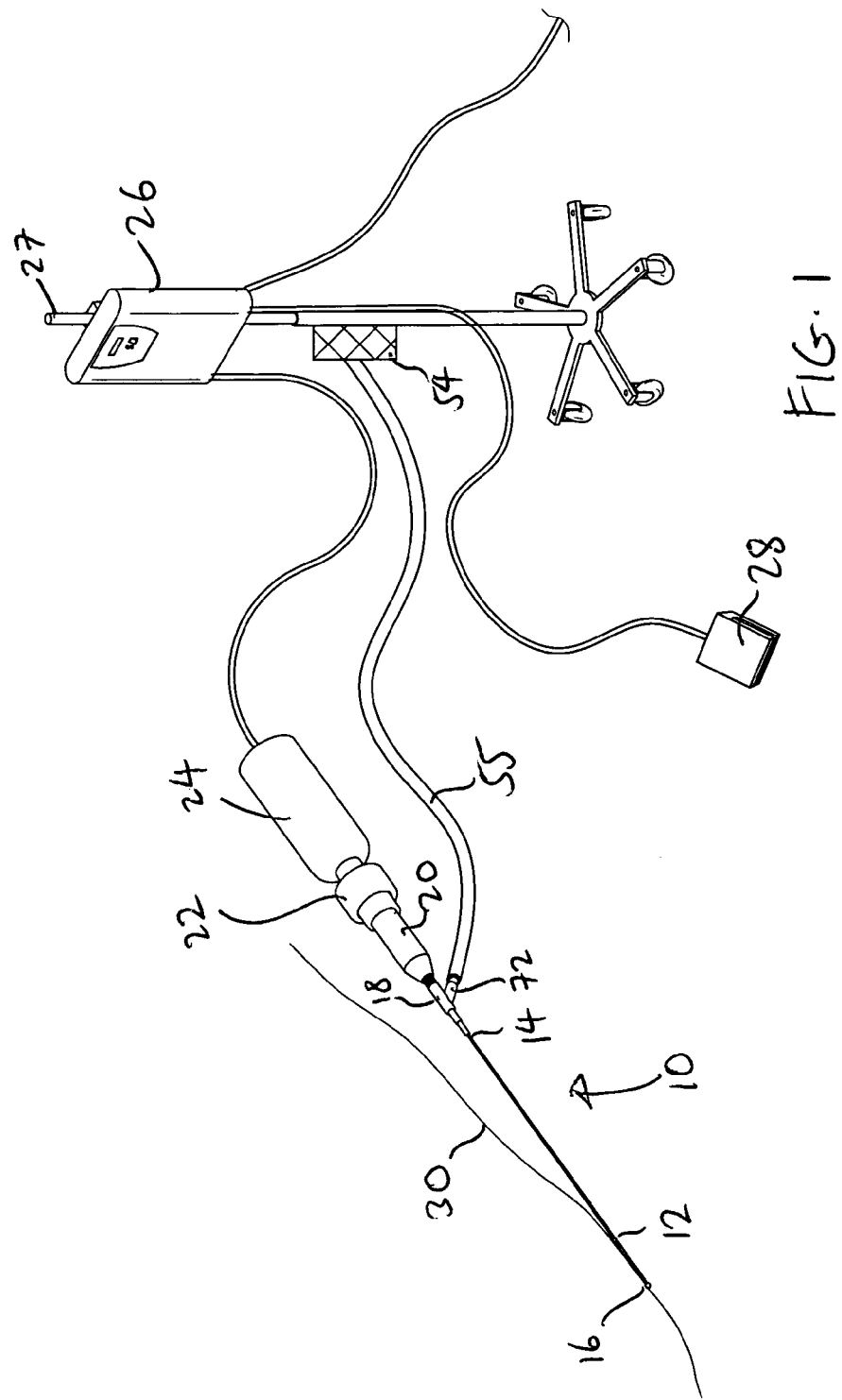
FIG. 1 is a perspective view of an ultrasound system according to the present invention.
Figure 2:
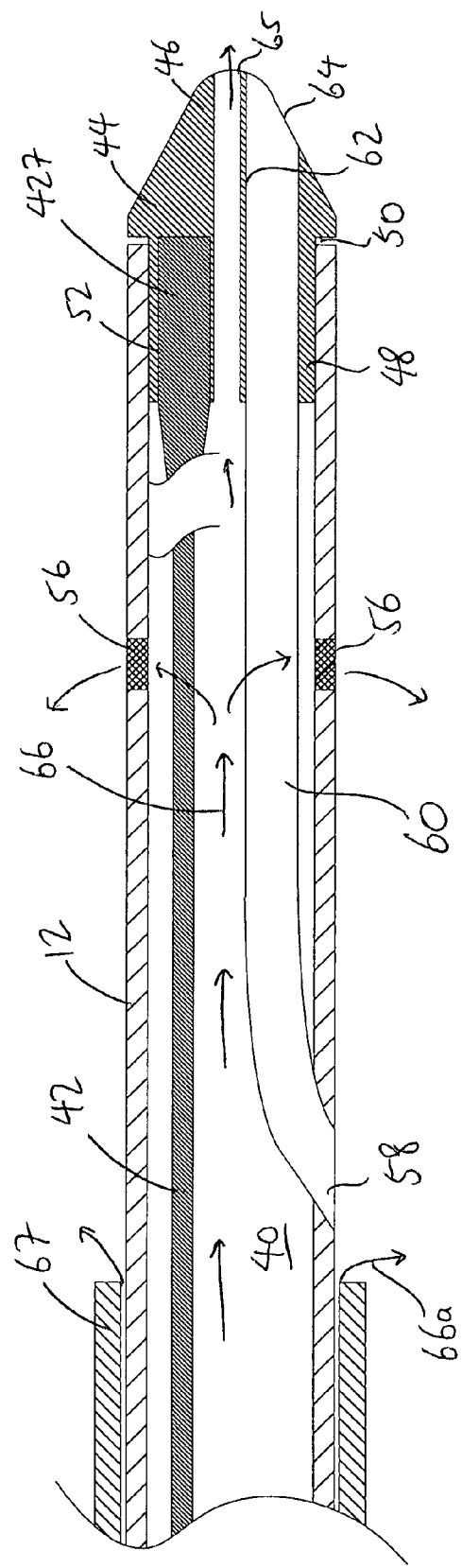
FIG. 2 is a cross-sectional view of the distal end of an ultrasound catheter that can be used with the system of FIG. 1.

FIGS. 1 and 2 illustrate an ultrasound system according to the present invention for use in ablating and removing occlusive material inside the vessel of an animal or human being. The ultrasound system includes an ultrasound catheter device 10 which has an elongate catheter body 12 having a proximal end 14, a distal end 16, and defining at least one lumen 40 extending longitudinally therethrough. The ultrasound catheter device 10 is operatively coupled at its proximal end 14, by way of a Y-connector 18, a catheter knob 20, and a slide collar 22, to an ultrasound transducer 24. The ultrasound transducer 24 is connected to a signal generator 26, which can be provided with a foot actuated on-off switch 28. The signal generator 26 can be supported by an IV pole 27. When the on-off switch 28 is depressed, the signal generator 26 sends an electrical signal to the ultrasound transducer 24, which converts the electrical signal to ultrasound energy. Such ultrasound energy subsequently passes through the catheter device 10 and is delivered to the distal end 16. A guidewire 30 may be utilized in conjunction with the catheter device 10, as will be more fully described below.

The catheter body 12 is formed of a flexible polymeric material such as nylon (Pebax™) manufactured by Atochimie, Cour be Voie, Hauts Ve-Sine, France. The flexible catheter body 12 is preferably in the form of an elongate tube having one or more lumens extending longitudinally therethrough. The catheter body 12 defines a main lumen 40. Extending longitudinally through the main lumen 40 is an elongate ultrasound transmission wire 42 having a proximal end which is removably connectable to the ultrasound transducer 24 via a sonic connector 76 (described below in connection with FIGS. 4 and 6) such that ultrasound energy will pass through the ultrasound transmission member 42. As such, when the foot actuated on-off switch 28 operatively connected to the ultrasound transducer 24 is depressed, ultrasound energy will pass through the ultrasound transmission member 42 to the distal end 16 of the catheter body 12.

A distal head 44 is affixed to the distal end 16 of the catheter body 12. In the embodiments shown, the distal head 44 has a generally blunt distal tip 46, and has a proximal portion 48 whose outer diameter is slightly less than the largest outer diameter of the distal head 44, so as to define an annular shoulder 50 that is placed in the open distal end of the catheter body 12 such that the proximal portion 48 of the distal head 44 is received inside the catheter body 12 in a manner where the outer surface of the catheter body 12 is flush with the outer surface of the distal head 44.

A guidewire port 58 is provided in the catheter body 12 at a location that is about 0.1 cm to 30 cm from the distal head 44. A guidewire lumen 60 extends from the guidewire port 58 through a bore 62 in the distal head 44 to a guidewire exit 64 at the tip 46 of the distal head 44.

The distal head 44 is preferably formed of a material that is rigid, is radio- dense, and has low-density. A material having such characteristics is desirable because the ultrasound energy that is delivered from a transducer 24 to the distal head 44 via the ultrasound transmission member 42 goes through severe bends in the patient's vasculature. These bends significantly impact the displacement at the distal head 44 and its ability to ablate atherosclerotic plaque. The distal head 44 provides an additional load so that a heavier distal head 44 will cause lower displacements. As a result, a distal head 44 made of a material that is rigid, is radio-dense, and which has low-density will improve the effectiveness of the ablation. As a non-limiting example, the material should have an average density that does not exceed 5 g/cm$^3$, or where the total mass of the distal head 44 does not exceed 0.015 grams.

As for the desired materials for the distal head 44, titanium alloys are preferable because they have the highest strength-to-weight ratios of any structural metals, and are corrosion resistant and biocompatible. Pure titanium has a density of 0.163 lb/in$^3$. Examples of desirable alloy elements for use with Titanium include Aluminum and Vanadium, such as in Ti-6AI-4V, which has tensile yield strength in the range of 130-150 ksi.

Although pure Aluminum is relatively weak, alloying with various elements yields significant strength improvements with minimal sacrifice in density. Pure Aluminum has a density of 0.097 lb/in$^3$. Examples of desirable alloying elements for Aluminum include Manganese, Silicon, and/or Magnesium, such as in 3, 4, 5 and 6 series Aluminum alloys. Tensile yield strengths of these common alloys range from 10-50 ksi.

Magnesium alloys are also preferable because they are extremely light, stable, abundant, and easy to machine. They have high specific strength and rigidity, with a very low density range of 0.064-0.066 lb/in$^3$, and UTS range of 22-55 ksi. Examples of desirable alloying elements that can be used with Magnesium include Aluminum and Zinc, such as in AZ31B for machined tips.

The ultrasound transmission wire 42 extends through the lumen 40, and is inserted into a bore 52 which extends longitudinally into the proximal portion 48 of the distal head 44. The distal end of the ultrasound transmission wire 42 is firmly held within the bore 52 by the frictional engagement thereof to the surrounding material of the distal head 44, or by other mechanical or chemical affixation means such as but not limited to weldments, adhesive, soldering and crimping. Firm affixation of the ultrasound transmission wire 42 to the distal head 44 serves to facilitate direct transmission of the quanta of ultrasonic energy passing through the ultrasound transmission wire 42 to the distal head 44. As a result, the distal head 44 and the distal end 16 of the catheter device 10 are caused to undergo ultrasonic vibration in accordance with the combined quanta of ultrasonic energy being transmitted through the ultrasound transmission wire 42.

In the preferred embodiment, the ultrasound transmission wire 42 may be formed of any material capable of effectively transmitting the ultrasonic energy from the ultrasound transducer 24 to the distal head 44, including but not necessarily limited to metal, plastic, hard rubber, ceramic, fiber optics, crystal, polymers, and/or composites thereof. In accordance with one aspect of the invention, all or a portion of the ultrasound transmission wire 42 may be formed of one or more materials which exhibit super-elasticity. Such materials should preferably exhibit super- elasticity consistently within the range of temperatures normally encountered by the ultrasound transmission wire 42 during operation of the catheter device 10. Specifically, all or part of the ultrasound transmission wire 42 may be formed of one or more metal alloys known as "shape memory alloys".

Examples of super-elastic metal alloys which are usable to form the ultrasound transmission wire 42 of the present invention are described in detail in U.S. Pat. No. 4,665,906 (Jervis); U.S. Pat. No. 4,565,589 (Harrison); U.S. Pat. No. 4,505,767 (Quin); and U.S. Pat. No. 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission wire 42 of the present invention operates, any and all of which super-elastic metal alloys may be usable to form the super-elastic ultrasound transmission wire 42.

The frontal portion of the Y-connector 18 is connected to the proximal end 14 of the catheter 10 using techniques that are well-known in the catheter art. An injection pump 54 or IV bag (not shown) or syringe (not shown) can be connected, by way of an infusion tube 55, to an infusion port or sidearm 72 of the Y-connector 18 (see FIG. 1). The injection pump can be used to infuse coolant fluid into and/or through the main lumen 40 of the catheter 10, with the coolant fluid exiting via irrigation outlets 56 (see FIGS. 2 and 5) provided adjacent the distal end 16 of the catheter 10. Such flow of coolant fluid may be utilized to prevent overheating of the ultrasound transmission wire 42 extending longitudinally through the main lumen 40. Such flow of the coolant fluid through the main lumen 40 of the catheter 10 also serves to bathe the outer surface of the ultrasound transmission wire 42, thereby providing for an equilibration of temperature between the coolant fluid and the ultrasound transmission wire 42. Thus, the temperature and/or flow rate of coolant fluid may be adjusted to provide adequate cooling and/or other temperature control of the ultrasound transmission wire 42. The irrigation fluid can include a pharmacological agent.

According to one embodiment of the present invention, the coolant fluid is preferably a refrigerated coolant fluid, preferably saline 0.9% NaCl. The refrigerated coolant fluid will be stored in a refrigerator or similar cooling unit at a temperature between 4 and 20 degrees Celsius (or between 40-72 degrees Fahrenheit) prior to use. The use of a low-temperature coolant fluid will be effective in maintaining the transmission wire 42 within the desired temperature range of 10-50 degrees Celsius. The refrigerated coolant fluid can be flowed through the main lumen 40 and exit the catheter body 12 via irrigation outlets 56 (see FIGS. 2 and 5) provided adjacent the distal end 16 of the catheter 10 and through the irrigation outlet 65 in the distal head 44. The numeral designation 66 in FIG. 2 can be used to represent the refrigerated coolant fluid and the microbubbles described below.

In addition to the foregoing, the injection pump 54 or syringe may be utilized to infuse a radiographic contrast medium into the catheter 10 for purposes of imaging, as described in greater detail below. Examples of iodinated radiographic contrast media which may be selectively infused into the catheter 10 via the injection pump are commercially available as Angiovist 370 from Berlex Labs, Wayne, N.J. and Hexabrix from Malinkrodt, St. Louis, Mo.

The proximal end of the Y-connector 18 is attached to the distal end of the catheter knob 20 by threadably engaging the proximal end of the Y-connector 18 inside a threaded distal bore (not shown) at the distal end of the catheter knob 20.

Referring also to FIGS. 4 and 6, the present invention further provides a sonic connector assembly that effectively connects the ultrasound transmission wire 42 to the transducer 24 in a manner which reduces step sonic amplification and provides a smooth connection transition of the transmission wire 42, thereby reducing the stress and fatigue experienced by the transmission wire 42. The sonic connector assembly includes a sonic connector 76 that functions to grip or otherwise retain the proximal end of the ultrasound transmission wire 42, and which can be removably connected to the transducer 24. In other words, the sonic connector 76 serves as an attaching element that couples the ultrasound transmission wire 42 to the transducer 24 in a manner which minimizes transverse movement at the connection area while maintaining longitudinal ultrasound energy propagation. In this regard, longitudinal vibrations are desirable, while transverse vibrations may cause breakage in the ultrasound transmission wire 42. The connection area between the ultrasound transmission wire 42 and the transducer horn 78 is critical because the vibrational energy passes through this connection. At this highest displacement point, longitudinal vibrations produce antinodes (maximum displacement/minimum stress), while transverse vibrations produce a node or area of maximum stress. Since the greatest amount of transverse motion occurs at the connection area between the ultrasound transmission wire 42 and the transducer horn 78, and because the cross-section of the ultrasound transmission wire 42 is small, reduction of transverse movements at the connection area between the ultrasound transmission wire 42 and the transducer horn 78 is crucial in protecting the integrity of the ultrasound transmission wire 42 and minimizing the potential for breakage of the ultrasound transmission wire 42. Such transverse vibrations can be minimized by placing transverse absorbers along the ultrasound transmission wire 42 at the connection area between the ultrasound transmission wire 42 and the transducer horn 78, as described below.

The sonic connector 76 is housed inside the proximal bore 84 of the catheter knob 20. The proximal bore 84 has a proximal opening into which the transducer horn 78 may be inserted to engage the sonic connector 76. A distal bore 88 is provided at the distal end of the catheter knob 20, with the distal bore 88 communicating with the proximal bore 84 via a channel 90. The sonic connector 76 has a front shaft 94 extending distally from a central portion 92. The sonic connector 76 also has a threaded stem 96 extending proximally from the central portion 92 to permit the distal end of the transducer horn 78 to be threadably screwed onto and removably attached to the sonic connector 76. The proximal end of the Y-connector 18 can be threadably engaged to the distal opening of the distal bore 88.

The distal end of the front shaft 94 has an inner bore (not shown) that terminates before the central portion 92. The proximal portion of the ultrasound transmission wire 42 extends through the channel 90 in the knob 20 and through the bores 84 and 88, and the proximal-most region 421 is dimensioned to be snugly fitted inside the inner bore of the front shaft 94. The proximal-most region 421 of the ultrasound transmission wire 42 is secured inside the inner bore of the front shaft 94 by welding, bonding, crimping, soldering, or other conventional attachment mechanisms.

A first absorber 98 is seated in the distal bore 88 and itself defines a bore that receives (i.e., circumferentially surrounds) the ultrasound transmission wire 42. In other words, the absorber 98 is positioned between the ultrasound transmission wire 42 and the bore 88. The absorber 98 can be made of an elastic material, and non-limiting examples include a polymer or rubber. Alternatively, the absorber 98 can be provided in the form of O-rings. The absorber 98 functions to absorb transverse micro-motions, thereby minimizing the undesirable transverse vibrations.

The sonic connector 76 can be provided with a partial thread and a flat proximal surface, which are important to providing a firm connection between the transducer horn 78 and the sonic connector 76. Specifically, referring to FIGS. 4 and 6, the threaded stem 96 has a thread 102 followed by a small unthreaded area 104 that separates the thread 102 from the proximal surface 106 of the central portion 92. This proximal surface 106 is flat, and interfaces with the flat distal surface of the transducer horn 78 (see FIG. 4), thereby allowing a manual connection and disconnection (screw and unscrew) between the transducer horn 78 and the sonic connector 76.

The present invention provides an ultrasound transmission wire 42 having a configuration that improves the delivery of ultrasound energy to the distal head 44 while minimizing stress and fatigue at the connection of the ultrasound transmission wire 42 to the sonic connector 76. In particular, the ultrasound transmission wire 42 of the present invention provides a proximal-most end that is connected with the sonic connector 76, with this proximal-most end having a greater diameter than the rest of the ultrasound transmission wire 42.

The ultrasound transmission wire 42 has a first proximal-most region 421, a second region 422 that extends distally from the distal end of the first region 421, a third region 423 that extends distally from the distal end of the second region 422, a fourth region 424 that extends distally from the distal end of the third region 423, a fifth region 425 that extends distally from the distal end of the fourth region 424, a sixth region 426 that extends distally from the distal end of the fifth region 425, and a seventh distal-most region 427 that extends distally from the distal end of the sixth region 426. As best shown in FIG. 2, the distal-most region 427 is received into the bore 52 of the distal head 44. The fourth region 424 and the fifth region 425 together define an intermediate region 428. The first region 421 has a diameter that is greater than the diameter of any of the other regions 422, 423, 424, 425, 426, 427, and the diameter of the first region 421 can be consistent throughout. The diameter of the second region 422 progressively tapers and decreases from its proximal end (where it transitions from the first region 421) to its distal end, where it transitions to the third region 423. The diameter of the third region 423 can be consistent throughout. The distal end of the third region 423 transitions to the proximal end of the intermediate region 428. The diameter of the intermediate region 428 progressively tapers and decreases from its proximal end (where it transitions from the third region 423) to its distal end, where it transitions to the sixth region 426. In this regard, the intermediate region 428 can be made up of any number of progressively decreasing-diameter regions itself, and the embodiment of FIG. 4 illustrates that the intermediate region 428 is made up of two such regions, the fourth region 424 and the fifth region 425. Thus, the diameter of the intermediate region 428 is smallest at its distal end (see 429), and in fact, the diameter at the distal end 429 of the intermediate region 428 can be the smallest along the length of the entire ultrasound transmission wire 42. The length of the intermediate region 428 is preferably between 5 to 150 cm, depending on the desired application. For example, the length of the region 428 can be about 40 cm if the catheter 10 is for use in coronary applications, and about 90 cm if the catheter 10 is for use with peripheral applications. Next, the diameter of the sixth region 426 progressively increases from its proximal end (where it transitions from the intermediate region 428) to its distal end, where it transitions to the seventh region 427. The diameter of the seventh region 427 can be consistent throughout. The diameter throughout the seventh region 427 is greater than the diameter of any part of the sixth region 426. In one embodiment of the present invention, the entire ultrasound transmission wire 42 (including all of its regions 421-427) can be formed in a single piece.

The first proximal-most region 421 is adapted to be attached to the sonic connector 76, which is in turn attached to the transducer 24. The first region 421 has a length that ranges between 0.005 and 5 inches, but is preferably between 0.01 and 0.5 inches. The first region 421 has a cross-sectional outer diameter that ranges between 0.01 and 0.06 inches, but is preferably between 0.035 and 0.045 inches. The third region 423 has a cross-sectional outer diameter that ranges between 0.02 and 0.05 inches, but is preferably about 0.030 inches. The third region 423 has a length that ranges between 20 to 140 cm, and preferably about 100 cm.

The significance of a larger-diameter proximal-most region 421 that is adapted to connect to the sonic connector 76 is as follows. The difference between the dimensions of the ultrasound transmission wire 42 and the horn of the transducer 24 creates a dimensional step which causes a large amplification of propagated ultrasound energy from the transducer 24 via the sonic connector 76 to the ultrasound transmission wire 42. In fact, both the transverse and longitudinal motions produced by the transducer 24 will be amplified by this dimensional step. In particular, the transverse motions create significant stress at the connection area between the ultrasound transmission wire 42 and the transducer 24. As a result, a smaller ultrasound transmission wire 42 (i.e., having a smaller diameter) would be more susceptible to breakage at the connection area. However, providing a larger-diameter ultrasound transmission wire 42 would not be feasible. For example, the proximal 10 to 20 inches of the ultrasound transmission wire 42 will typically be outside the patient during an interventional procedure, and this proximal portion is often subjected to bends while a physician handles the catheter 10. These bends would cause a larger-diameter ultrasound transmission wire 42 to experience greater acoustical losses than a smaller-diameter ultrasound transmission wire 42. As a result of these considerations, the present invention provides a novel configuration for the ultrasound transmission wire 42 where (I) the proximal-most region 421 has the greatest diameter to minimize breakage at the connection area, (ii) portions of the intermediate region 428 (e.g., the region 425) have the smallest diameter to improve propagation of ultrasound energy, and (iii) the distal regions 426, 427 have a greater diameter than the intermediate region 428 to facilitate greater efficiency in the transmission of ultrasound energy from the ultrasound transmission wire 42, to improve the strength of the ultrasound transmission wire 42, and to minimize breakage of the ultrasound transmission wire 42. In particular, increasing the cross-section of the ultrasound transmission wire 42 at its distal end provides a larger cross-sectional area to tolerate stress associated with the attachment of distal-most region 427 to the distal head 44.

The tapering in some of the regions (e.g., 423, 424, 425, 426) provides a continuous and smooth transition for the amplification of ultrasound energy without steps, which helps improve the stability of the ultrasound transmission wire 42.

The present invention also provides the use of microbubbles to enhance the cavitational effect and improve the ultrasound ablation. According to the present invention, microbubbles 66 (see FIG. 2) can be injected with a cooling fluid or irrigant during an ultrasound procedure when ultrasound energy is being delivered to the distal head 44. The microbubbles 66 that can be used in the present invention can be embodied in the form of agitated saline solution, or made of gas encapsulated in shells. Examples of commercially available microbubbles include but are not limited to OPTISON™ sold by Mallincrodt Medical, DEFINITY™ sold by Dupont Pharmaceuticals, LEVOVIST™ and IMAGENT™ sold by Schering, SONO VUE™ sold by Bracco Imaging, and PB-127 ™ sold by Point-Biomedical. The microbubbles 66 can be introduced through the infusion port or sidearm 72 of the Y-connector 18 by an injection pump. The microbubbles 66 are delivered into and/or through the main lumen 40 of the catheter 10 and exit via irrigation outlets 56 (see FIGS. 2 and 5) provided adjacent the distal end 16 of the catheter 10 and through the irrigation outlet 65 in the distal head 44. The microbubbles 66a can also be delivered in front of the distal head 44 via a conventional guiding catheter 67 (see FIG. 2) or any other sheath that surrounds the catheter 10.

The microbubbles 66, 66a improve the cavitational effect. In particular, the reciprocating movement of the distal tip 46 of the catheter 10 in a fluid (i.e., blood) creates cavities or bubbles to create a transitory phenomenon or mechanical effect called cavitation. It produces an instantaneous stress estimated at many thousands of atmospheres, and a significantly higher temperature within a cavitation threshold, at a very small area in front of the distal tip 46. If the catheter is placed against atherosclerotic material, this cavitation will cause ablation of the material. Adding microbubbles 66, 66a in front of the distal tip 46 where cavitation is taking place will increase the number of bubbles at the distal tip 46, thereby enhancing cavitation. In other words, the introduction of additional microbubbles increases the cavitational effect without changing or adding to the construction of the catheter 10.

Thus, the ultrasound system according to present invention provides structural components that address two of the general problems encountered by the known ultrasound systems and devices. For instance, effective transmission of ultrasound energy is achieved by the novel transmission wire 42 and the sonic connector 76. In addition, the transmission wire 42 is cooled by the refrigerated coolant fluid and the use of microbubbles. Further, the introduction of microbubbles to the distal tip 46 of the catheter 10 enhances cavitation.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method for disrupting an occlusion in a blood vessel, the method comprising:
    providing a catheter having:
        a catheter body having a wall, a proximal end, a distal end, and irrigation outlets through the wall near the distal end of the body;
        a lumen extending through the catheter body;
        a distal head disposed within and extending out from the distal end of the body, wherein the head has an irrogation outlet aperture that extends through the head; and
        an ultrasound transmission member comprising:
            a proximal-most first region with a first-region diameter;
            a second region that extends distally from the first region wherein the second region narrows from a second-region proximal end to a second-region distal end;
            a third region that extends distally from the second region wherein the third region has a constant third-region diameter less than the first-region diameter;
            an intermediate region comprising:
                a fourth region that extends distally from the third region; and
                a fifth region that extends distally from the fourth region;
                wherein the intermediate region progressively narrows from a fourth-region proximal end to a fifth-region distal end and wherein the narrow-most diameter of the ultrasound transmission member occurs at the fifth-region distal end,
            a sixth region that extends distally from the fifth region wherein the sixth region progressively widens from a sixth-region proximal end to a sixth-region distal end;
            a distal-most seventh region that extends distally from the sixth region at a constant seventh region diameter;
    positioning the catheter in a blood vessel such that the distal head is adjacent the occlusion;
    providing microbubbles in irrigation fluid;
    transmitting ultrasound energy through the ultrasound transmission member to the distal head, the energy being of sufficient power to create fluid cavitation near the distal head within the blood vessel, the cavitation disrupting the occlusion into multiple occlusion fragments; and
    during the transmission of ultrasound energy, flowing the irrigation fluid and microbubbles through at least the lumen and the irrigation outlet aperture and into the blood vessel near the occlusion, whereby the presence of microbubbles in the irrigation fluid enhances said cavitation.

2. The method of claim 1, further including removing the occlusion fragments that are outside the ultrasound catheter in the blood vessel through the ultrasound catheter.

3. The method of claim 1, further including:
    providing an irrigation inlet aperture at a proximal end of the catheter; and
    introducing the irrigation fluid through the aperture.

4. The method of claim 1, further including:
    providing a side aperture piercing the wall proximal to the distal end of the catheter.

5. The method of claim 4, further comprising flowing the irrigation fluid and microbubbles through the side aperture.

6. The method of claim 1, wherein the irrigation fluid is refrigerated.

7. The method of claim 1, wherein the microbubbles are made from agitated saline solution.

8. The method of claim 1, wherein the microbubbles are made of gas encapsulated in shells.

9. The method of claim 1, further including causing the microbubbles to contact the occlusion.

10. The method of claim 1 further including providing a pharmacological agent in the irrigation fluid.

11. The method of claim 1 wherein the ultrasound member has distal end disposed near the distal end of the catheter and a proximal end disposed near the proximal end of the catheter.

12. The method of claim 1 wherein the catheter further comprises a guidewire lumen and the distal head further comprises a guidewire aperture substantially aligned with the guidewire lumen.

13. The method of claim 1 wherein the distal head has at least two different diameters and the distal diameter is greater than the proximal diameter.

14. A method for disrupting an occlusion in a blood vessel comprising:
    providing a catheter comprising a catheter body having a wall, a proximal end, a distal end, and irrigation outlets through the wall near the distal end of the body;

an ultrasound transmission member extending through the lumen and comprising:
  a proximal-most first region with a first-region diameter;
  a second region that extends distally from the first region wherein the second region narrows from a second-region proximal end to a second-region distal end;
  a third region that extends distally from the second region wherein the third region has a consistent third-region diameter less than the first-region diameter;
  an intermediate region comprising:
    a fourth region that extends distally from the third region; and
    a fifth region that extends distally from the fourth region;
    wherein the intermediate region progressively narrows from a fourth-region proximal end to a fifth-region distal end and wherein the narrow-most diameter of the ultrasound transmission member occurs at the fifth-region distal end,
  a sixth region that extends distally from the fifth region wherein the sixth region progressively widens from a sixth-region proximal end to a sixth-region distal end;
  a distal-most seventh region that extends distally from the sixth region at a consistent seventh region diameter;
  a distal end;
  a distal head disposed within and extending out from the distal end of the catheter body and having an irrigation outlet aperture, wherein the distal end of the transmission member couples to the distal head;
positioning the catheter in a blood vessel such that the distal head is adjacent the occlusion;
introducing an irrigation fluid that contains microbubbles, through the lumen, the irrigation outlet aperture and into the vessel at or near the distal head; and
transmitting ultrasound energy through the ultrasound transmission member to create cavitation in a liquid containing the microbubbles, the microbubbles enhancing the cavitation.

15. The method of claim 14 wherein the ultrasound member has distal end disposed near the distal end of the catheter and a proximal end disposed near the proximal end of the catheter.

16. The method of claim 14 wherein the catheter further comprises a guidewire lumen and the distal head further comprises a guidewire aperture substantially aligned with the guidewire lumen.

17. The method of claim 14 wherein the distal head has at least two different diameters and the distal diameter is greater than the proximal diameter.

18. The method of claim 14, wherein positioning the ultrasound catheter comprises using a guiding catheter.

19. The method of claim 14, wherein positioning the ultrasound catheter comprises using a guidewire.

20. The method of claim 14, wherein positioning the ultrasound catheter comprises using both a guiding catheter and a guidewire.

21. The method of claim 14, wherein the irrigation fluid is refrigerated.

22. The method of claim 21, wherein the refrigerated irrigation fluid is delivered during an interventional procedure.

23. The method of claim 21, further including providing a pharmacological agent in the refrigerated irrigation fluid.

24. The method of claim 21, further comprising refrigerating the irrigation fluid to a temperature between 40 and 60 degrees Fahrenheit.

25. A method for disrupting an occlusion in a blood vessel comprising:
providing an ultrasound catheter wherein providing an ultrasound catheter comprises
  providing
    a catheter part having a catheter body, a lumen extending through the catheter body, an ultrasound transmission member with a distal end extending through the lumen, distally located side irrigation outlets, and a distal head having an irrigation outlet aperture, the ultrasound transmission member comprising:
      a proximal-most first region with a first-region diameter;
      a second region that extends distally from the first region wherein the second region narrows from a second-region proximal end to a second-region distal end;
      a third region that extends distally from the second region wherein the third region has a consistent third-region diameter throughout its length less than the first-region diameter;
      an intermediate region comprising:
        a fourth region that extends distally from the third region; and
        a fifth region that extends distally from the fourth region;
        wherein the intermediate region progressively narrows from a fourth-region proximal end to a fifth-region distal end and wherein the narrow-most diameter of the ultrasound transmission member occurs at the fifth-region distal end,
      a sixth region that extends distally from the fifth region wherein the sixth region progressively widens from a sixth-region proximal end to a sixth-region distal end;
      a distal-most seventh region that extends distally from the sixth region with a consistent seventh region diameter through its length;
    coupling the ultrasound transmission member to the distal head; and
    coupling the catheter part to the distal head,
positioning the ultrasound catheter in a blood vessel such that the distal head is adjacent the occlusion;
transmitting ultrasound energy through the ultrasound transmission member to form bubbles in a liquid at the distal head; and
introducing an irrigation fluid that contains microbubbles from a location outside the blood vessel through the lumen and exiting at least the irrigation outlet aperture in the distal head, the microbubbles enhancing cavitation, wherein the irrigation fluid is different than the liquid.

26. The method of claim 25, wherein the liquid comprises blood.

27. The method of claim 25, wherein the irrigation fluid is saline solution.

* * * * *